US008727989B2

(12) United States Patent
Baba

(10) Patent No.: US 8,727,989 B2
(45) Date of Patent: May 20, 2014

(54) AUTOMATIC DIAGNOSIS SUPPORT APPARATUS, ULTRASONIC DIAGNOSIS APPARATUS, AND AUTOMATIC DIAGNOSIS SUPPORT METHOD

(75) Inventor: Tatsuro Baba, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 619 days.

(21) Appl. No.: 12/824,696

(22) Filed: Jun. 28, 2010

(65) Prior Publication Data

US 2010/0331688 A1    Dec. 30, 2010

(30) Foreign Application Priority Data

Jun. 30, 2009 (JP) ................. 2009-156318

(51) Int. Cl.
*A61B 8/00* (2006.01)
(52) U.S. Cl.
USPC ........... 600/441; 600/407; 600/409; 600/453; 600/454; 600/455; 382/128; 382/130; 382/131
(58) Field of Classification Search
USPC ................ 600/407, 409, 437, 441, 453, 454; 382/131
See application file for complete search history.

(56) References Cited

U.S. PATENT DOCUMENTS

| | | | |
|---|---|---|---|
| 7,513,872 B2 | 4/2009 | Baba et al. | |
| 2003/0097056 A1* | 5/2003 | Suzuki et al. | 600/409 |
| 2006/0052704 A1 | 3/2006 | Baba et al. | |
| 2009/0138263 A1* | 5/2009 | Shozakai et al. | 704/243 |
| 2012/0027278 A1* | 2/2012 | Chaney et al. | 382/131 |

FOREIGN PATENT DOCUMENTS

JP   2004-222864   8/2004

OTHER PUBLICATIONS

Hisato Nakajima, et al. "The Examination of New Standard for Liver Transplantation Adaptation using the Mahalanobis-Taguchi System", Quality Engineering, vol. 14, No. 4, Aug. 2006. pp. 550-558 (With English Abstract).
Tatsuji Kanetaka, et al. "MT System and Diagnosis of Liver Disease (2) Case of Special Medical Examination analysed by T Method (3)", Quality Engineering, vol. 15, No. 4, Aug. 2007. pp. 52-57 (With English Abstract).
Taro Tetsumi, et al. "Estimation of Optimal Settings by MT Method—Optimum Adjustment of Roller Spacing in a Spinning Machine", Quality Engineering, vol. 16, No. 3, Jun. 2008. pp. 93-100 (With English Abstract).

(Continued)

*Primary Examiner* — Baisakhi Roy
(74) *Attorney, Agent, or Firm* — Oblon, Spivak, McClelland, Maier & Neustadt, L.L.P.

(57) ABSTRACT

Certain embodiments provide an automatic diagnosis support apparatus includes extracting a plurality of parameters associated with a predetermined object by using medical information acquired by a medical image diagnosis apparatus and extracting the plurality of parameters for each disease associated with a disable-bodied person by using medical information associated with the disable-bodied person, calculating a ruler associated with each disease case by executing an MT system using the plurality of parameters for each disease associated with the disable-bodied person, calculating a distance between the object and a state space of the disable-bodied person associated with the each disease by executing the MT system using a plurality of parameters associated with the object, determining a disease type of the object by using the ruler and a distance between the object and a state space of a disable-bodied person, and generating diagnosis support information based on the determination result.

22 Claims, 11 Drawing Sheets

(56) References Cited

OTHER PUBLICATIONS

Hiroki Matsui, et al. "Assessment of a Training Protocol of Echocardiographic Examination: Accuracy and Reproducibility", J. Med Ultrasonics, vol. 29, No. 6, 2002. pp. 537-544 (With English Abstract).

Katsusuke Kajihara, et al. "Questionnaire Survey on the State of Routine Echocardiographic Examinations in Japan: Second Report", J Med Ultrasonics, vol. 32, No. 3, 2005. pp. 329-337 (With English Abstract).

Sachiko Watanabe, et al. "Influence of Aging on Cardiac Function Examines by Echocardiography", J Med Ultrasonics, vol. 29, No. 2, 2002. pp. 145-151 (With English Abstract).

Office Action issued Aug. 20, 2013 in Japanese Patent Application No. 2009-156318 (with English-language translation).

Toshiyuki Furukawa, Computer Diagnosing, Kyoritsu Shuppan Co., Ltd., Dec. 15, 1982, pp. 1-4.

Hisato Makajima, et al., "Predictive Evaluation and Efficiency of Medical Examination based on Mahalanobis Taguchi System Method," Japan public-health magazine, vol. 46, No. 5, May 15, 1999, pp. 351-363.

Office Action issued Apr. 1, 2014, in Japanese Patent Application No. 2009-156318, filed Jun. 30, 2009 (with English-language Translation).

\* cited by examiner

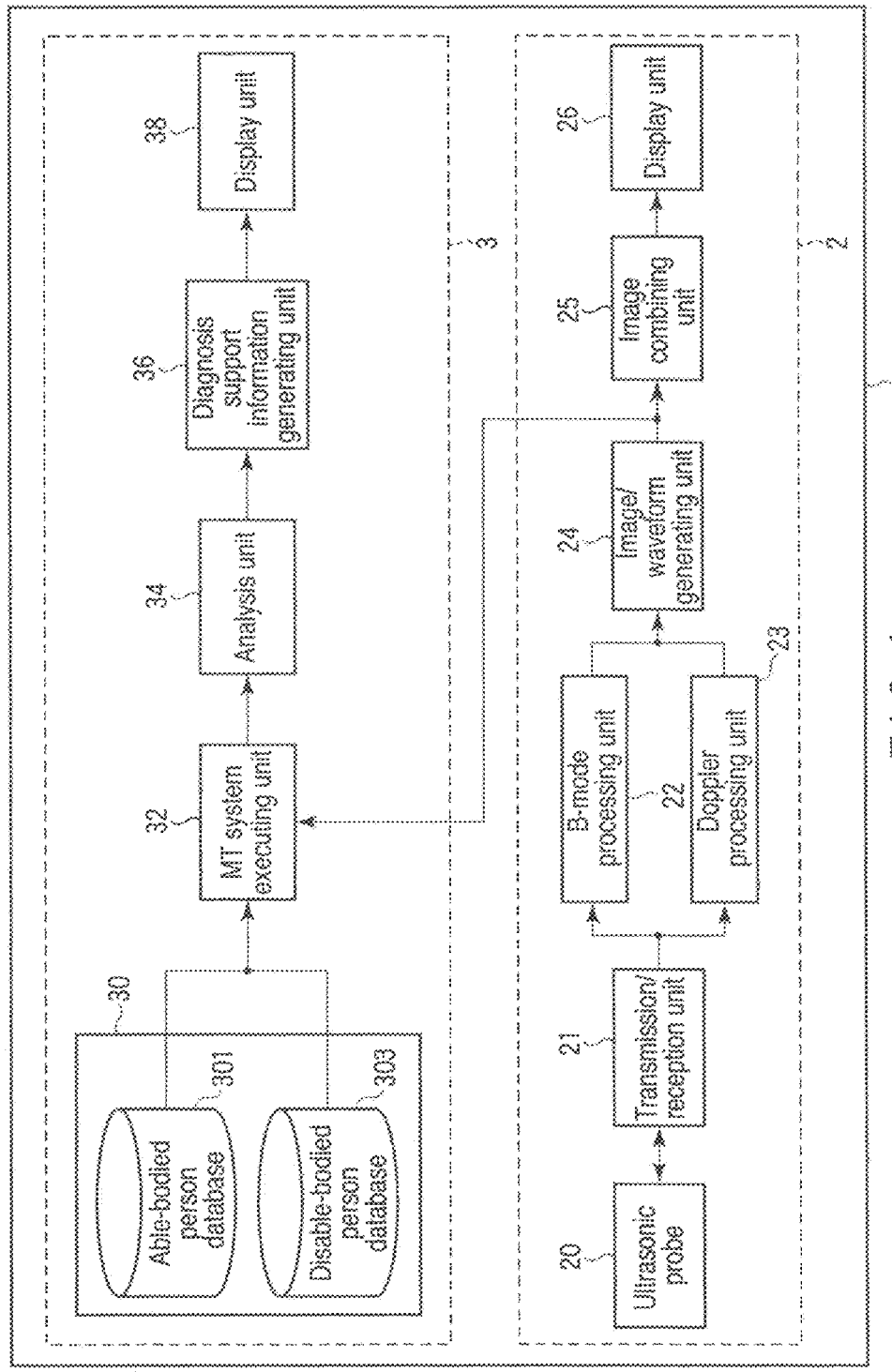
F I G. 1

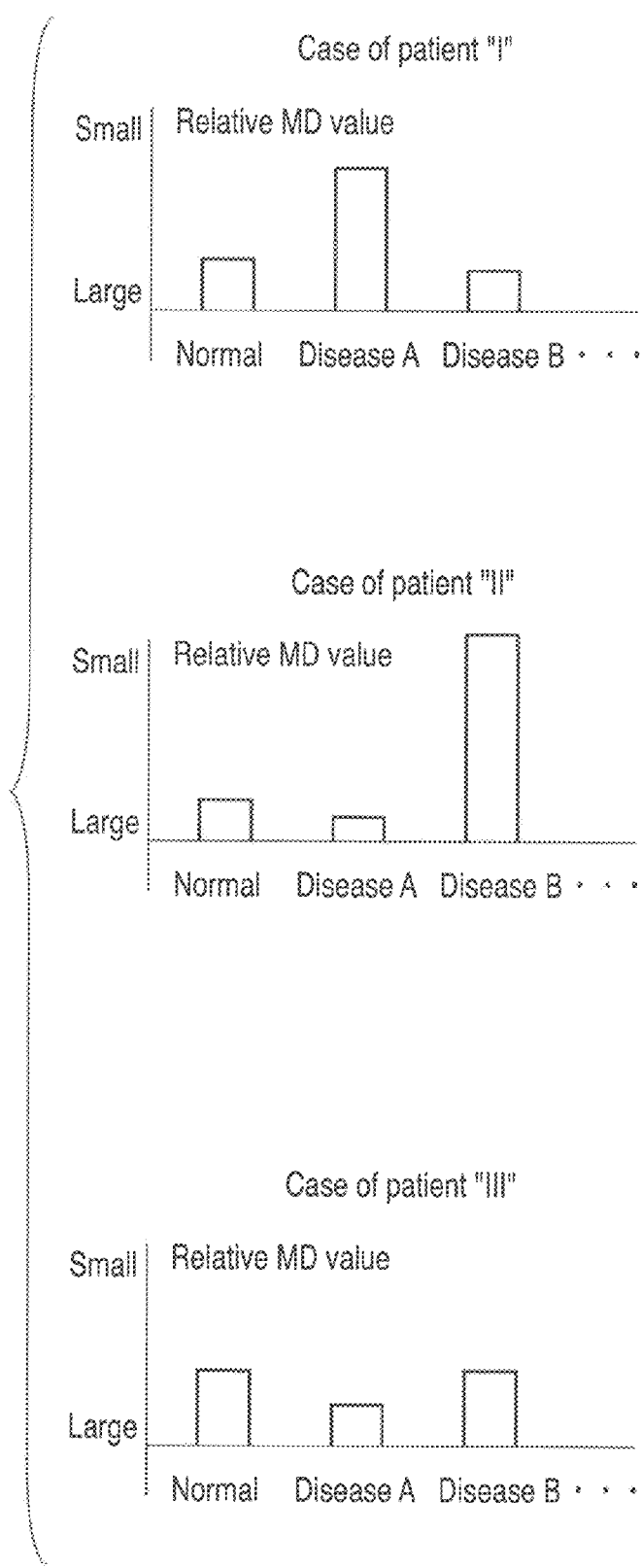

AUTOMATIC DIAGNOSIS SUPPORT APPARATUS, ULTRASONIC DIAGNOSIS APPARATUS, AND AUTOMATIC DIAGNOSIS SUPPORT METHOD

CROSS-REFERENCE TO RELATED APPLICATIONS

This application is based upon and claims the benefit of priority from Japanese Patent Application No. 2009-156318, filed Jun. 30, 2009; the entire contents of which are incorporated herein by reference.

FIELD

Embodiments described herein relate generally to an automatic diagnosis support apparatus, an ultrasonic diagnosis apparatus, and an automatic diagnosis support method.

BACKGROUND

The embodiments relate to computer-aided diagnosis (CAD) using images and, more particularly, to a computer-aided diagnosis using a plurality of interpretation results based on different algorithms.

Computer-aided diagnosis is a technique of presenting the position of a focus candidate detected from an input digital image or an quantitative analysis result using the computer on an image in an easily understandable manner by using an image pattern recognition technique in order to reduce the load of image diagnosis on a doctor or technician, assuming that the doctor makes final determination in diagnosis. This technique is used, for example, for lung cancer screening using chest X-ray pictures and CT images for mass screening, automatic breast cancer mammography screening systems, stomach cancer detection systems, circulatory organ Doppler diagnosis in ultrasonic image diagnosis, and the like.

Recently, automatic diagnosis support apparatuses using such computer-aided diagnosis have used a technique called the MT (Mahalanobis-Taguchi) system. The MT system is a technique of forming a new criterion by synthesizing polyvariant items (multivariates) in quality engineering. The types of such technique include the MT (Mahalanobis Taguchi) method, T (Taguchi) method, MTA (Mahalanobis Taguchi Ajoint) method, and TS (Taguchi Schmitt) method. About five years have passed since this MT system was begun to be applied to normality/abnormality identification/determination. Recently, a special application of the system has been made to implement identification using factorial effect patterns of SN ratios in discriminating the type of liver disease.

The conventional automatic diagnosis support apparatus, however, has the following problems.

The mainstream image pattern recognition techniques include a neural network method, principal component analysis method, and multivariate analysis method (regression analysis/factor analysis method), and have no consistency in interaction, model pattern extraction, parameter variation range, main component selection scheme, and the like. For this reason, no general-purpose analysis technique has been established yet, and hence the image pattern recognition technique lacks in credibility and reproducibility.

In addition, a liver disease type discrimination method using the MT system analyzes factor patterns which increase the distances of individual cases in abnormal patterns based on the state space of able-bodied persons. For this reason, even if, for example, this method allows suitable automatic determination in the case of the liver, it is not clear that the same method is useful for the discrimination of other diseases (versatile).

BRIEF DESCRIPTION OF THE DRAWINGS

FIG. 1 is a block diagram showing the arrangement of an automatic diagnosis support system 1 according to an embodiment;

FIG. 8 is a view showing an example of histograms as diagnosis support information generated in step S5;

DETAILED DESCRIPTION

Figure 2:
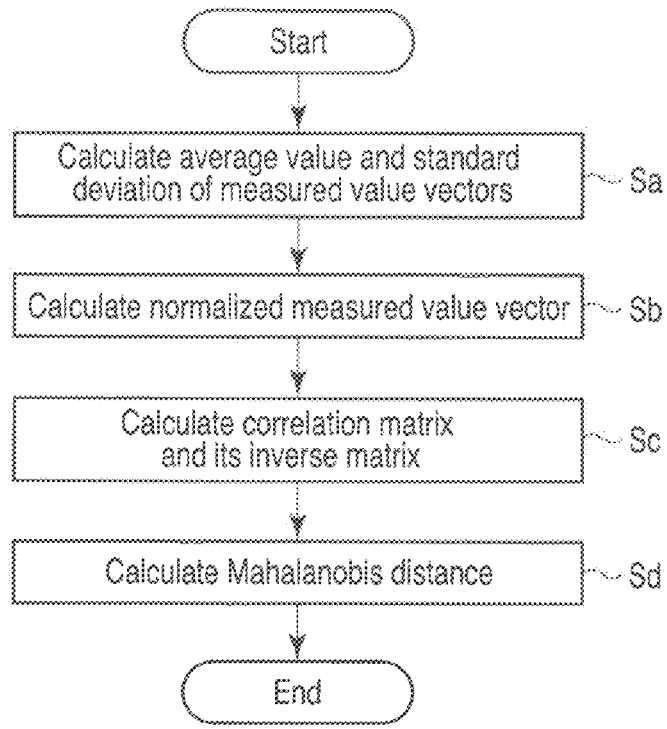
FIG. 2 is a flowchart showing a general procedure for calculating Mahalanobis distances.

Certain embodiments provide an automatic diagnosis support apparatus comprising an extraction unit configured to extract a plurality of parameters associated with a predetermined object by using medical information associated with the object which is acquired by a medical image diagnosis apparatus and to extract the plurality of parameters for each disease associated with a disable-bodied person by using medical information associated with the disable-bodied person and acquired in advance, a calculation unit configured to calculate a ruler associated with each disease case by executing an MT system using the plurality of parameters for each disease associated with the disable-bodied person as item factors and to calculate a distance between the object and a state space of the disable-bodied person associated with each disease by executing the MT system using a plurality of parameters associated with the object as item factors, a determination unit configured to determine a disease type of the object by using the ruler associated with each disease case and a distance between the object and a state space of a disable-bodied person associated with each disease, a support information generating unit configured to generate diagnosis support information based on the determination result, and a display unit configured to display the diagnosis support information in a predetermined form.

This embodiment will be described below with reference to the views of the accompanying drawing. Note that the same reference numerals denote constituent elements having substantially the same functions and arrangements in the following description, and a repetitive description will be made only when required.

FIG. 1 is a block diagram showing the arrangement of an automatic diagnosis support system 1 according to this embodiment. As shown in FIG. 1, the automatic diagnosis support system 1 includes an ultrasonic diagnosis apparatus 2 and an automatic diagnosis support apparatus 3. Note that the ultrasonic diagnosis apparatus 2 and automatic diagnosis support apparatus 3 constituting the automatic diagnosis support system 1 may be used singly or in combination with each other. In addition, the automatic diagnosis support apparatus 3 itself may be made to function as the automatic diagnosis support system 1 by incorporating the ultrasonic diagnosis apparatus 2 in the automatic diagnosis support apparatus 3. The arrangements of the ultrasonic diagnosis apparatus 2 and automatic diagnosis support apparatus 3 will be described below.

(Ultrasonic Diagnosis Apparatus)

The ultrasonic diagnosis apparatus 2 includes an ultrasonic probe 20, a transmission/reception unit 21, a B-mode processing unit 22, a Doppler processing unit 23, an image/waveform generating unit 24, an image combining unit 25, and a display unit 26.

The ultrasonic probe 20 includes a plurality of piezoelectric transducers which generate ultrasonic waves based on driving signals from the transmission/reception unit 21 and convert reflected waves from an object into electrical signals, a matching layer provided for the piezoelectric transducers, and a backing member which prevents ultrasonic waves from propagating backward from the piezoelectric transducers. When the ultrasonic probe 20 transmits an ultrasonic wave to an object P, the transmitted ultrasonic wave is sequentially reflected by a discontinuous surface of acoustic impedance of internal body tissue, and is received as an echo signal by the ultrasonic probe 20. The amplitude of this echo signal depends on an acoustic impedance difference on the discontinuous surface by which the echo signal is reflected. The echo produced when a transmitted ultrasonic pulse is reflected by a moving blood flow or tissue is subjected to a frequency shift depending on the velocity component of the moving body in the ultrasonic transmission direction due to a Doppler effect.

The transmission/reception unit 21 includes a trigger generating circuit, delay circuit, and pulser circuit (none of which are shown). The pulser circuit repetitively generates rate pulses for the formation of transmission ultrasonic waves at a predetermined rate frequency fr Hz (period: 1/fr sec). The delay circuit gives each rate pulse a delay time necessary to focus an ultrasonic wave into a beam and determine transmission directivity for each channel. The trigger generating circuit applies a driving pulse to the probe 20 at the timing based on this rate pulse.

The transmission/reception unit 21 includes an amplifier circuit, A/D converter, and adder (none of which are shown). The amplifier circuit amplifies an echo signal received via the probe 20 for each channel. The A/D converter gives the amplified echo signals delay times necessary to determine reception directivities. The adder then performs addition processing for the signals. With this addition, a reflection component is enhanced from a direction corresponding to the reception directivity of the echo signal to form a composite beam for ultrasonic transmission/reception in accordance with reception directivity and transmission directivity.

The B-mode processing unit 22 receives an echo signal from the transmission/reception unit 21, and performs logarithmic amplification, envelope detection processing, and the like for the signal to generate B-mode image data whose signal intensity is expressed by a luminance level.

The Doppler processing unit 23 frequency-analyzes velocity information from the echo signal received from the transmission/reception unit 21, extracts a blood flow or tissue owing to a Doppler effect and a contrast medium echo component, and obtains blood information such as mean velocities, variances, powers, and the like at multiple points. The obtained blood flow information is sent to the image generating circuit 25, and is displayed in color as a mean velocity image, a variance image, a power image, and a combined image thereof on the monitor 14.

The image/waveform generating unit 24 converts the scanning line signal string obtained by ultrasonic scanning into a scanning line signal string in a general video format typified by a TV format, thereby generating an ultrasonic diagnosis image or Doppler waveform as a display image. The image/waveform generating unit 24 includes a memory to store image data, and can perform three-dimensional image reconstruction processing and the like. This unit allows the operator to call up an image recorded during examination after diagnosis. Note that data before it is input to the image/waveform generating unit 24 is sometimes called "raw data".

The image combining unit 25 combines the image received from the image/waveform generating unit 24 with character information of various types of parameters, scale marks, and the like, and outputs the resultant signal as a video signal to the monitor 14. The image combining unit 25 also stores a three-dimensional reconstruction program, an image processing program, and the like. These programs are activated in accordance with instructions from the operator and the like.

The display unit 26 displays morphological information and blood flow information in the living body as images based on video signals from the image combining unit 25.

Note that in addition to the above constituent elements, the ultrasonic diagnosis apparatus 2 includes an input unit including various types of switches, buttons, a trackball, a mouse, and a keyboard which are used to input, to the apparatus 2, various types of instructions, conditions, an instruction to set a region of interest (ROI), various types of image quality condition setting instructions, and the like from an operator, and a transmission/reception unit for transmitting and receiving data to and from other apparatuses via a network.

(Automatic Diagnosis Support Apparatus)

The automatic diagnosis support apparatus 3 includes a database unit 30, an MT system executing unit 32, an analysis unit 34, a diagnosis support information generating unit 36, and a display unit 38.

The database unit 30 includes an able-bodied person database 301 and a disable-bodied person database 303.

The able-bodied person database 301 stores a plurality of automatically measured values associated with a plurality of able-bodied persons, B-mode image data acquired by the ultrasonic diagnosis apparatus, Doppler measurement data acquired by the ultrasonic diagnosis apparatus, image data acquired by medical image diagnosis apparatuses other than the ultrasonic diagnosis apparatus (for example, an X-ray computed tomography apparatus, magnetic resonance imaging apparatus, X-ray diagnosis apparatus, and nuclear medicine diagnosis apparatus), ECG waveforms, and the like.

Note that an able-bodied person is a person determined by a doctor to "have no disease related to cardiac function" at the time of the acquisition of measured values.

The disable-bodied person database 303 stores, for each disease, a plurality of automatically measured values associated with a plurality of disable-bodied persons, B-mode image data acquired by the ultrasonic diagnosis apparatus, Doppler measurement data acquired by the ultrasonic diagnosis apparatus, image data acquired by medical image diagnosis apparatuses other than the ultrasonic diagnosis apparatus (for example, an X-ray computed tomography apparatus, magnetic resonance imaging apparatus, X-ray diagnosis apparatus, and nuclear medicine diagnosis apparatus), ECG waveforms, and the like. Note that a disable-bodied person is a person determined by a doctor to "have some kind of disease to be discriminated by the automatic diagnosis support function (to be described later)". In the MT system, therefore, disable-bodied persons do not belong to the state space of able-bodied persons. Cardiac diseases include, for example, hypercardia, heart infarction, mitral regurgitation, aortic regurgitation, septal defect, and tachycardia-bradycardia syndrome. However, the types of diseases need not be limited to them. The present embodiment can also be applied to diseases other than the above diseases.

The MT system executing unit 32 extracts parameters from the respective types of measured values (diagnosis indexes), image patterns, and Doppler waveforms stored in the able-bodied person database 301, generates the multivariate state space of able-bodied persons using the extracted parameters as item factors, and calculates Mahalanobis distances as rulers or indexes for the measurement of nearness to the respective diseases. The MT system executing unit 32 also extracts parameters from the respective types of measured values (diagnosis indexes), image patterns, and Doppler waveforms stored in the disable-bodied person database 303, generates the multivariate state spaces of disable-bodied persons, for the respective diseases, using the extracted parameters as item factors, and calculates Mahalanobis distances as rulers or indexes for the measurement of nearness to the respective diseases. Furthermore, the MT system executing unit 32 extracts parameters from the automatically measured values (diagnosis indexes) associated with a predetermined patient, image patterns, and Doppler waveforms which are automatically measured by the ultrasonic diagnosis apparatus 2, and calculates the Mahalanobis distances of the patient from the state spaces of the respective diseases by using the extracted parameters as item factors.

The analysis unit 34 determines whether a predetermined patient has a normal or abnormal health condition, and if the patient has an abnormal health condition, determines the type of disease, based on the Mahalanobis distances of the patient from the state spaces of the respective diseases and the rulers calculated for the state spaces of the respective diseases.

FIG. 2 is a flowchart showing a general procedure for calculating Mahalanobis distances. As shown in FIG. 2, first of all, the MT system executing unit 32 calculates the average value and standard deviation σj of measured value vectors xij=(x1j, x2j, . . . , xmj) for each measurement item j (1≤j≤n) (step Sa). The MT system executing unit 32 then normalizes each measured value vector xij by using the calculated average value and standard deviation σj of xij according to equation (1), and calculates normalized measured value vectors Xij=(X1j, X2j, . . . , Xmj) (step Sb).

$$X_{ij} = (x_{ij} - \overline{x}_j)/\sigma_i \quad (1)$$

$$\sigma = \sqrt{\frac{1}{n}\sum_i^n (x_i - \overline{x})^2} \quad (2)$$

Note that a population o is operated (normalized) according to equation (2) so as to make the average value of Mahalanobis distances equal to 1. The processing in steps Sa and Sb is performed for all (n) measurement items.

The MT system executing unit 32 then calculates a correlation matrix R and its inverse matrix $R^{-1}$ according to equations (3) and (4) given below by using the measured value vectors Xij normalized for each item (step Sc).

$$R = \begin{bmatrix} 1 & r_{12} & \ldots & r_{1k} \\ r_{21} & 1 & \ldots & r_{2k} \\ \ldots & \ldots & \ldots & \ldots \\ r_{k1} & r_{k2} & \ldots & 1 \end{bmatrix} \quad (3)$$

$$R^{-1} = \begin{bmatrix} a_{11} & a_{12} & \ldots & a_{1k} \\ a_{21} & a_{22} & \ldots & a_{2k} \\ \ldots & \ldots & \ldots & \ldots \\ a_{k1} & a_{k2} & \ldots & a_{kk} \end{bmatrix} \quad (4)$$

Here, the correlation function of l=1=n is as following.

$$r_{ij} = (\Sigma x_{il} \cdot x_{jl})/n$$

The inverse matrix is calculated by a versatile method.

The MT system executing unit 32 calculates squares $D^2$ of Mahalanobis distances (MD) according to equations (5), (6), (7), and (8) given below by using the inverse matrix $R^{-1}$ of the correlation matrix (step Sd).

$$U = [u_1 \, u_2 \ldots u_k] \quad (5)$$

Here, $u_1, u_2, \ldots, u_k$ are unit spaces.

$$U_j = \frac{u_j - m_j}{\sigma_j} \quad (6)$$

$U_j$ is normalized by unit space of each item.

$$D^2 = \frac{1}{k} \cdot U \cdot R^{-1} \cdot U^T \quad (7)$$

$$= \frac{1}{k} \sum_{i,j=1}^{k} a_{ij} \cdot \left(\frac{u_i - m_i}{\sigma_i}\right) \cdot \left(\frac{u_j - m_j}{\sigma_j}\right)$$

Here, $$\frac{1}{n}(D_1^2 + D_2^2 + \ldots + D_n^2) = 1 \quad (8)$$

Figure 3:
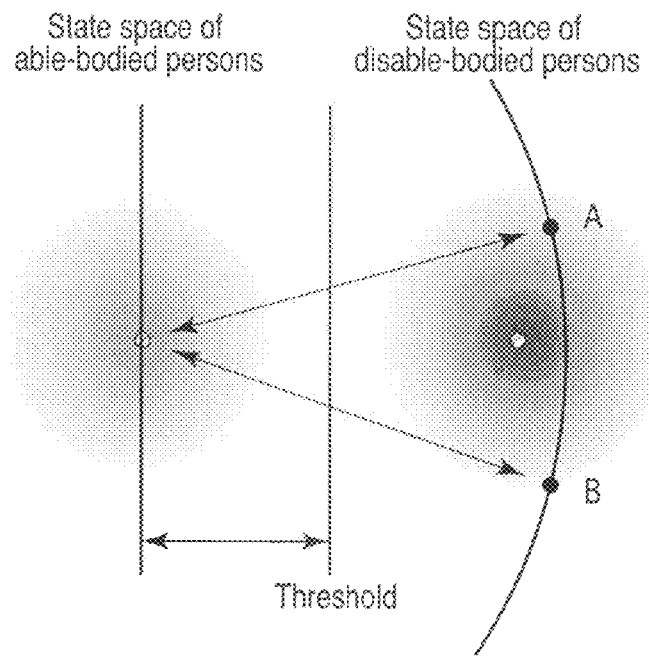
FIG. 3 is a view for explaining a concept of determination processing using Mahalanobis distances.

With this calculation, as shown in, for example, FIG. 3, the MT system executing unit 32 calculates the Mahalanobis distances between the state space of able-bodied persons and patients A and B, and compares the distances with a predetermined threshold, thereby determining whether patients A and B are able-bodied persons.

Note that it is possible to calculate SN ratios by using equations (9) to (14) given below.

$$\text{total variation } S_T = D_1^2 + D_2^2 + \ldots + D_n^2 \quad (9)$$

$$\text{magnitude of signal } r = M_1^2 + M_2^3 + \ldots + M_n^2 \quad (10)$$

$$\text{variation of proportional term } S_\beta = \frac{(M_1 \cdot D_1 + M_2 \cdot D_2 + \ldots M_n \cdot D_n)^2}{r} \quad (11)$$

$$\text{variation of error } S_e = S_T - S_\beta \quad f = n - 1 \quad (12)$$

$$\text{deviation of error } V_e = S_e / (n-1) \quad (13)$$

$$\text{SN ratio } \eta = 10 \cdot \log \frac{(S_\beta - V_e)/r}{V_e} \quad (14)$$

Figure 4:
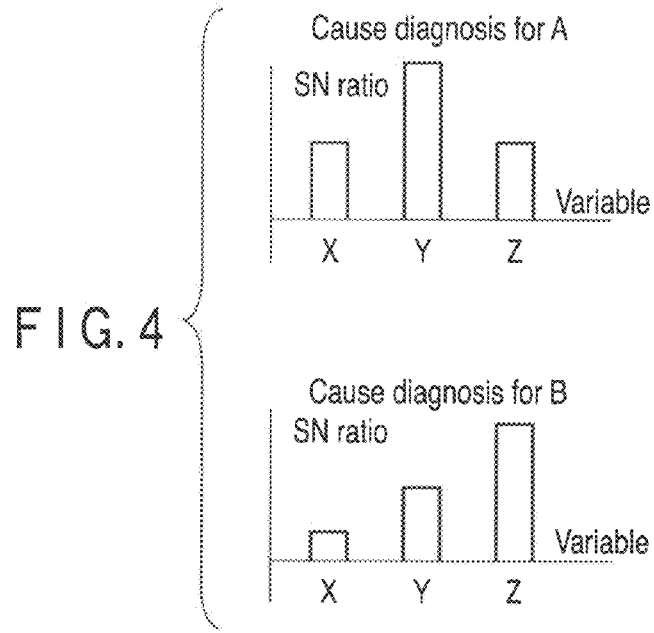
FIG. 4 is a view for explaining cause diagnosis using SN ratios in the MT system.

It is possible to generate a histogram like that shown in FIG. 4 by using the above SN ratios and make etiologic diagnosis.

The diagnosis support information generating unit 36 generates diagnosis support information such as a radar chart RC indicating the risk of having each disease (the higher the similarity, the higher the risk) based on the result of analysis processing executed by the analysis unit 34.

The display unit 38 displays the diagnosis support information generated by the diagnosis support information generating unit 36 in a predetermined form.

(Automatic Diagnosis Support Function)

The automatic diagnosis support function which the automatic diagnosis support system 1 has will be described next. This function is configured to extract parameters by using the automatically measured values (diagnosis indexes), image patterns, waveforms, and the like obtained by automatic measurement by a medical image diagnosis apparatus such as an ultrasonic diagnosis apparatus, generate rulers for the respective disease cases using the parameters as item factors in the MT system, determine whether a predetermined patient (i.e., a patient (object) who is unknown whether he/she is in a normal or abnormal condition, or if he/she is in an abnormal condition, unknown about the type of disease) has a normal or abnormal health condition, or if he/she has an abnormal condition, the type of disease, and display the result as diagnosis support information in a predetermined form.

Figure 5:
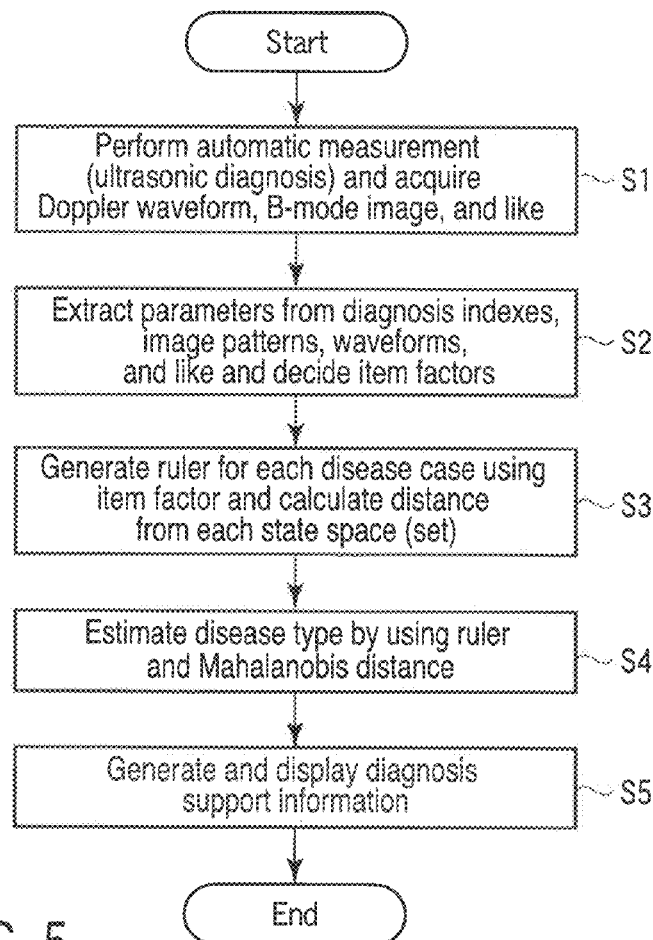
FIG. 5 is a flowchart showing a procedure for processing (automatic diagnosis support processing) based on an automatic diagnosis support function according to this embodiment.

FIG. 5 is a flowchart showing a procedure for processing (automatic diagnosis support processing) based on this automatic diagnosis support function. The contents of processing executed in each step will be described below. Assume that in this embodiment, the operation of the automatic diagnosis support apparatus 3 is controlled to start in response to, for example, the completion of the acquisition of medical information by the ultrasonic diagnosis apparatus 2.

[Automatic Measurement•Doppler Waveform•Acquisition of B-Mode Image and Like: Step S1]

First of all, automatic measurement on a predetermined patient is executed by using the ultrasonic diagnosis apparatus 2 or the like. This automatic measurement obtains an ECG waveform, Doppler waveform, B-mode image, and the like (step S1).

[Parameter Extraction•Decision of Item Factors: Step S2]

The MT system executing unit 32 then calculates various parameters to be item factors in the MT system by using the ECG waveforms, Doppler waveforms, B-mode images, respective diagnosis indexes, and the like acquired in step S1. More specifically, the MT system executing unit 32 calculates the pattern recognition data of an acquired ultrasonic image (e.g., the two-dimensional correlation function of the B-mode image), the waveform pattern recognition data obtained by using a differential-integral method or the like, and the diagnosis indexes based on the ECG waveform and Doppler measurement (step S2).

Note that the calculation of parameters to be set as item factors need not be limited to the information acquired in step S1. For example, it is possible to use the image data acquired in advance by another modality or the data acquired by past diagnosis.

[Calculation of Ruler for Each Disease Case and Mahalanobis Distance of Patient: step S3]

The MT system executing unit 32 extracts parameters from various measured values (diagnosis indexes), image patterns, and Doppler waveforms stored in the able-bodied person database 301, generates the multivariate state space of able-bodied persons by using the extracted parameters as item factors, and calculates a Mahalanobis distance (ruler). The MT system executing unit 32 also extracts parameters from various measured values (diagnosis indexes), image patterns, and Doppler waveforms stored in the disable-bodied person database 303, generates the multivariate state space of disable-bodied persons for each disease by using the extracted parameters as item factors, and calculates a Mahalanobis distance (ruler) for each disease. The MT system executing unit 32 further calculates the Mahalanobis distances of the patient from the respective state spaces corresponding to the respective diseases and from the state space of able-bodied persons by using the respective parameters calculated in step S2 as item factors (step S3).

Note that the MT system executing unit 32 preferably normalizes the ruler associated with each disease and the distance between the patient and the state space of disable-bodied persons for each disease.

[Determination of Disease Type: Step S4]

The analysis unit 34 determines, based on the Mahalanobis distance of the predetermined patient from the state space associated with each disease and the ruler calculated for the state space associated with each disease, whether the patient has a normal or abnormal health condition, and if he/she has an abnormal condition, determines the disease type (step S4).

Figure 6:
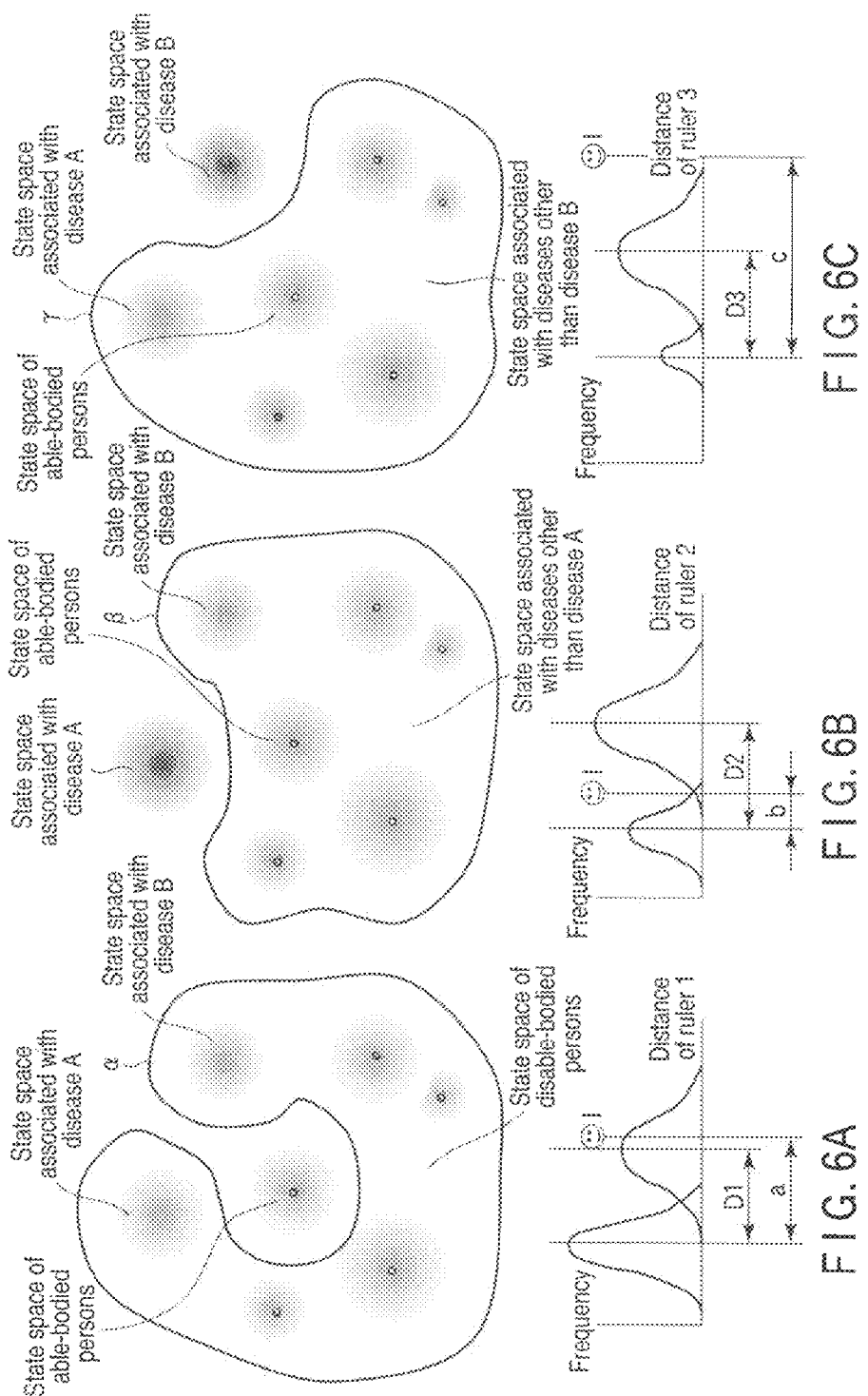
FIGS. 6A, 6B, and 6C are views for explaining a concept of determination processing executed by an analysis unit 34 in step S4.

FIGS. 6A, 6B, and 6C are views for explaining a concept of determination processing executed by the analysis unit 34 in step S4. When, for example, determining whether a given person is an able-bodied person as shown in FIG. 6A, the analysis unit 34 calculates a relative distance a/D1 by using a Mahalanobis distance a of patient I from the state space of able-bodied persons and a distance (ruler) D1 between a set α of the state spaces of persons (disable-bodied persons) who are not able-bodied persons and the state space of the able-bodied persons. As the relative distance a/D1 obtained as a result of the calculation approaches 0 (zero), the analysis unit 34 determines that the possibility of corresponding to the item (in this case, being an able-bodied person) is high.

Likewise, when determining whether patient I corresponds to disease A, the analysis unit 34 calculates a relative distance b/D2 by using a Mahalanobis distance b of patient I from the state space associated with disease A and a distance (ruler) D2 between a set β of state spaces which do not correspond to disease A and the state space associated with disease A. As the relative distance b/D2 obtained as a result of the calculation approaches 0 (zero), the analysis unit 34 determines that the possibility of corresponding to the item (in this case, being disease A) is high. The same applies to the determination of other diseases.

Figure 7:
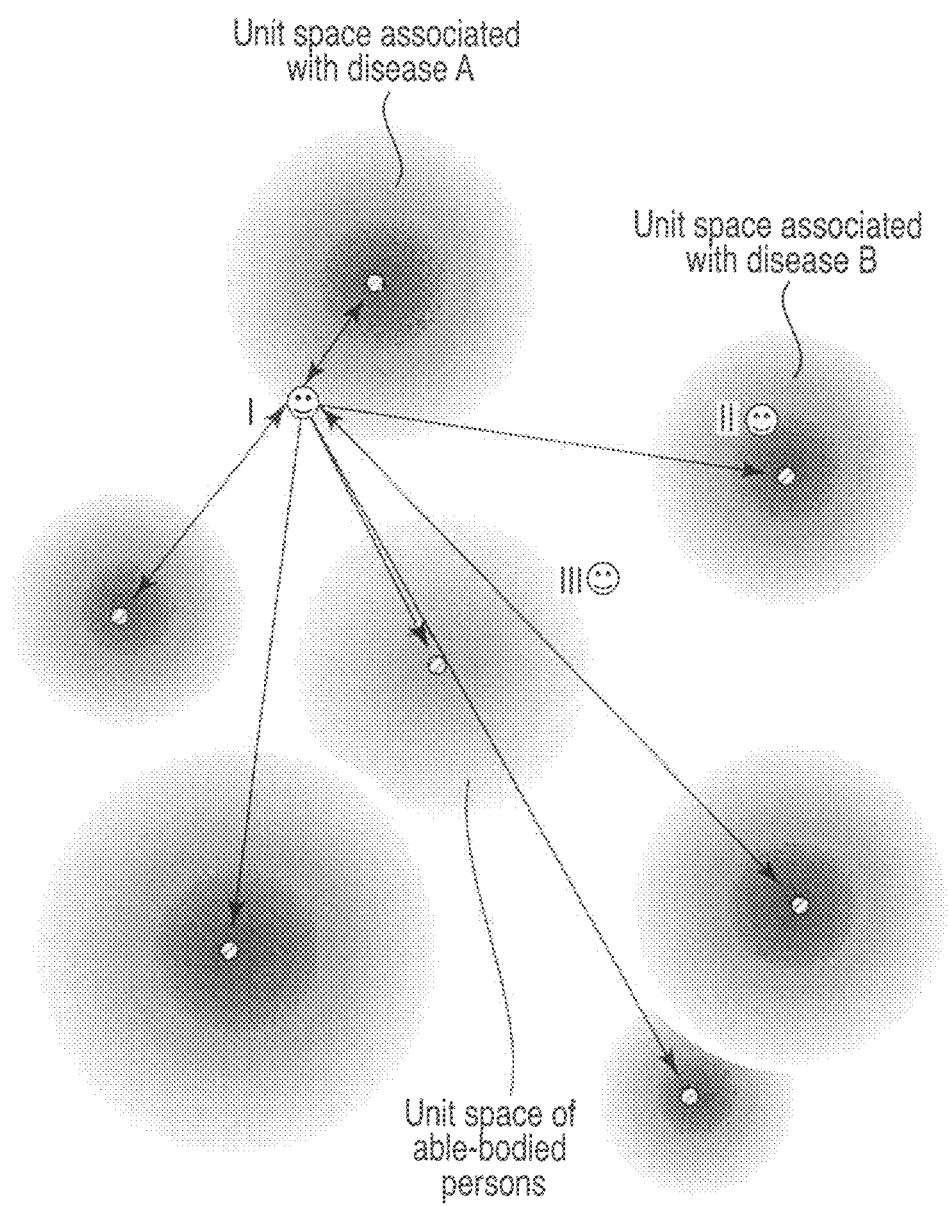
FIG. 7 is a view for explaining the nearness of patient I from each state space (unit space) with reference to a relative distance.

The result of such determination processing makes it clear how patient I is near each state space (unit space) with reference to a relative distance, as shown in FIG. 7. In the case shown in FIG. 7, patient I is nearest to the unit space associated with disease A, and hence is likely to have disease A. In addition, patient II is likely to have disease B. Patient III is nearest to the state space of able-bodied persons, and hence is likely to have no disease.

[Generation•Display of Diagnosis Support Information: Step S5]

The diagnosis support information generating unit 36 then generates a histogram, radar chart, and the like as diagnosis support information by using the result of the normality/abnormality determination and the determination result for each disease type which are executed in step S4 (step S5).

FIG. 8 is a view showing an example of histograms as diagnosis support information generated in step S5. FIG. 8 shows the relative Mahalanobis distances (relative MD values) of objects I, II, and III from the respective items (the respective diseases) including "normal", "disease A", and "disease B".

Figure 9A:
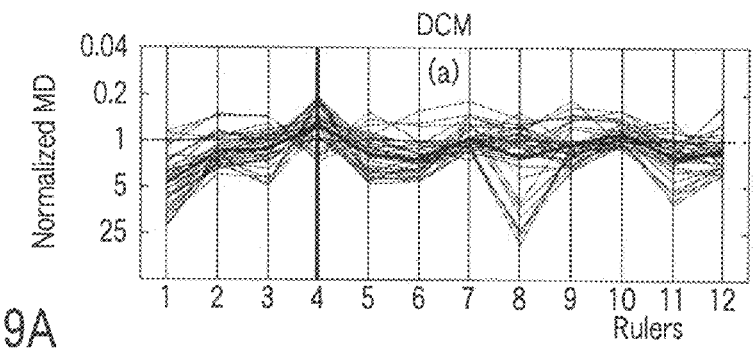
FIGS. 9A and 9B are graphs showing a histogram for DCM cases in which good results have been obtained and a histogram for AR cases which have been difficult to discriminate.
Figure 9B:
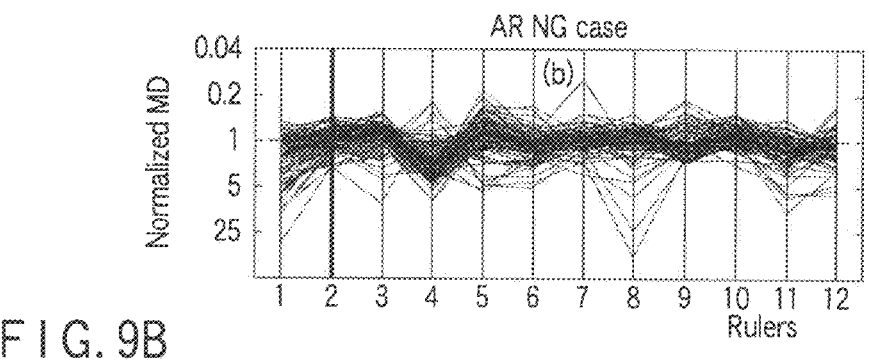

As more concrete example, FIGS. 9A and 9B show a histogram for DCM cases for which good results have been obtained and a histogram for AR cases which have been difficult to discriminate. The numbers 1 to 12 on the abscissa in each of FIGS. 9A and 9B indicate rulers corresponding to items such as "able-bodied person", "AR", "AS-moderate", and "stenocardia", and the ordinate represents the distance. FIG. 9A shows DCM disease data corresponding to ruler 4. The thick line represents the average value of the data. In the case of DCM, a peak appears at ruler 4. Obviously, the disease is properly discriminated. In contrast, FIG. 9B shows AR disease data corresponding to ruler 2. Likewise, the thick line represents the average value of the data. In this case, peaks appear at rulers 5 and 10 rather than ruler 2. Obviously, the disease is not properly discriminated.

Figure 10:
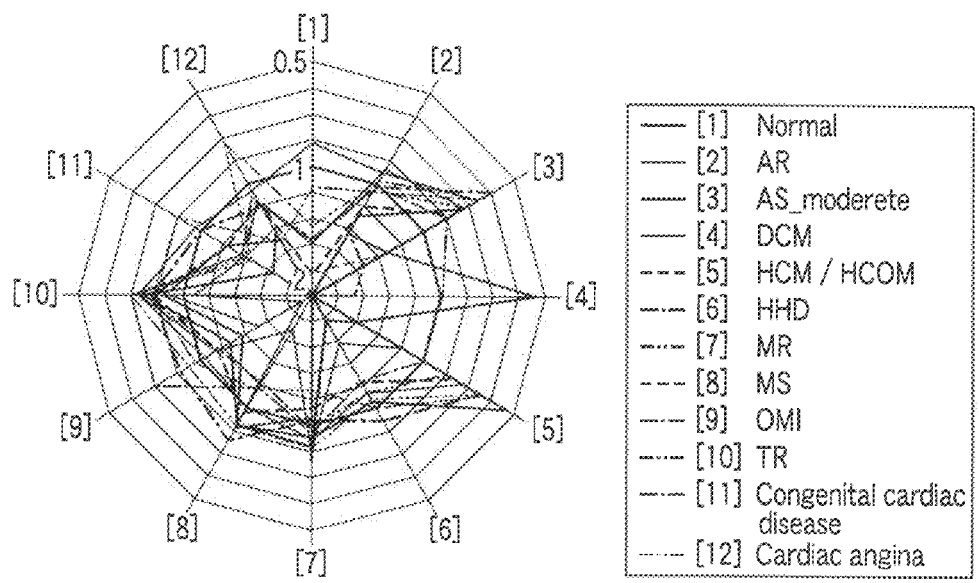
FIG. 10 is a view showing another example of a radar chart as diagnosis support information generated in step S5.

FIG. 10 a view showing an example of a radar chart (a radar chart indicating the average values of distances between able-bodied person [1] and diseases [2] to [12]) as diagnosis support information generated in step S5. The nearer to the circumference, the nearer to each unit space. Obviously, good results are obtained regarding DCM and AS-moderate exhibit, but a peak appears on another disease. That is, the disease is not properly discriminated.

Figure 11:
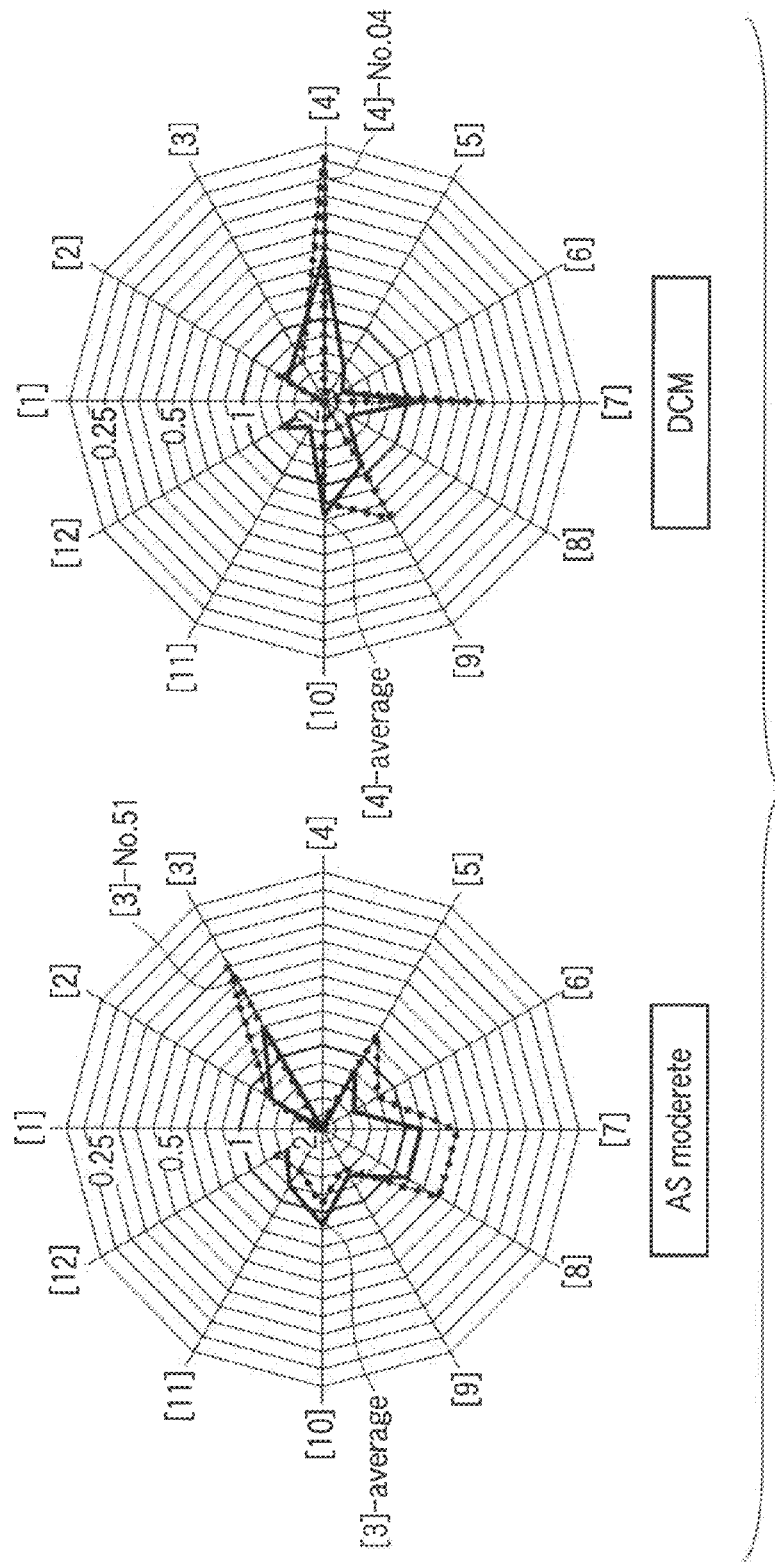
FIG. 11 is a view showing still another example of a radar chart as diagnosis support information generated in step S5.

FIG. 11 is a view showing another example of a radar chart as diagnosis support information generated in step S5. FIG. 11 shows data exhibiting high congruence with the average values of AS-moderate data and DCM data indicating relatively proper disease discrimination. Of the diagnosis indexes used for these analyses, E wave velocity and the ratio between E wave velocity and annulus velocity greatly contribute to disease discrimination. It is also obvious that it is highly possible to discriminate a disease by using only the information obtained by Doppler diagnosis.

(Example)

An example of automatic diagnosis support processing will be described next.

In order to improve the practicability of the automatic diagnosis support technique, an attempt has been made to discriminate the type of cardiac disease as well as performing discrimination between an able-bodied person and a disable-bodied person. A study has been made to examine the possibility of the above operation using the MT system based on the diagnosis data of the same doctor over past several years.

Diagnosis index data corresponding to about 3,000 persons which were obtained cardiac echo examination on able-bodied persons and disable-bodied persons were classified into 13 types including "able-bodied person", "AR", "AS-moderate", "DCM", "HCM/DCM", "HHD", "MR", "MS", "TR", "OMI", "congenital cardiac disease", "stenocardia", and "unclassifiable". The number of able-bodied person data was finally set to 900 by adjusting a unit space using the Jackknife method. The number of 11 types of disease-specific data except for "unclassifiable" data were about 40 to 300. Analysis was performed with a combination of about 20 types of diagnosis indexes obtained from ages, sexes, heart rates, M-mode images, and B-mode images other than Doppler measurement values. In this case, no waveform pattern recognition data were used. With this analysis, separation performance was evaluated through factorial effect analysis on specific diseases based on the unit space of able-bodied persons.

Figure 12:
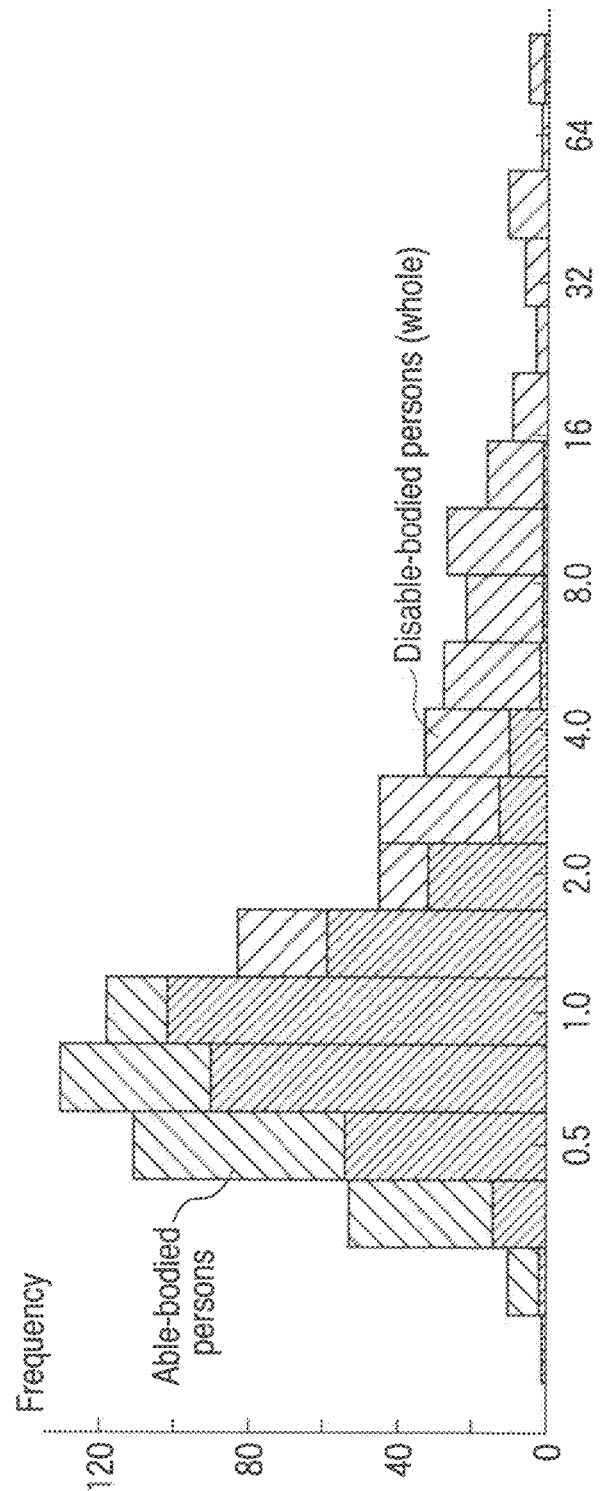
FIG. 12 is a view showing a histogram for the Mahalanobis distances (MD values) of able-bodied persons and disable-bodied persons (all diseases)

FIG. 12 shows the Mahalanobis distance (MD value) histogram of able-bodied persons and disable-bodied persons (all diseases). As is obvious, the space of able-bodied persons and the space of disable-bodied persons overlap each other and cannot be discriminated. It was found that it was difficult to discriminate able-bodied persons from disable-bodied persons (all diseases) by using only simple measurement indexes without any waveform pattern recognition data.

Figure 13:
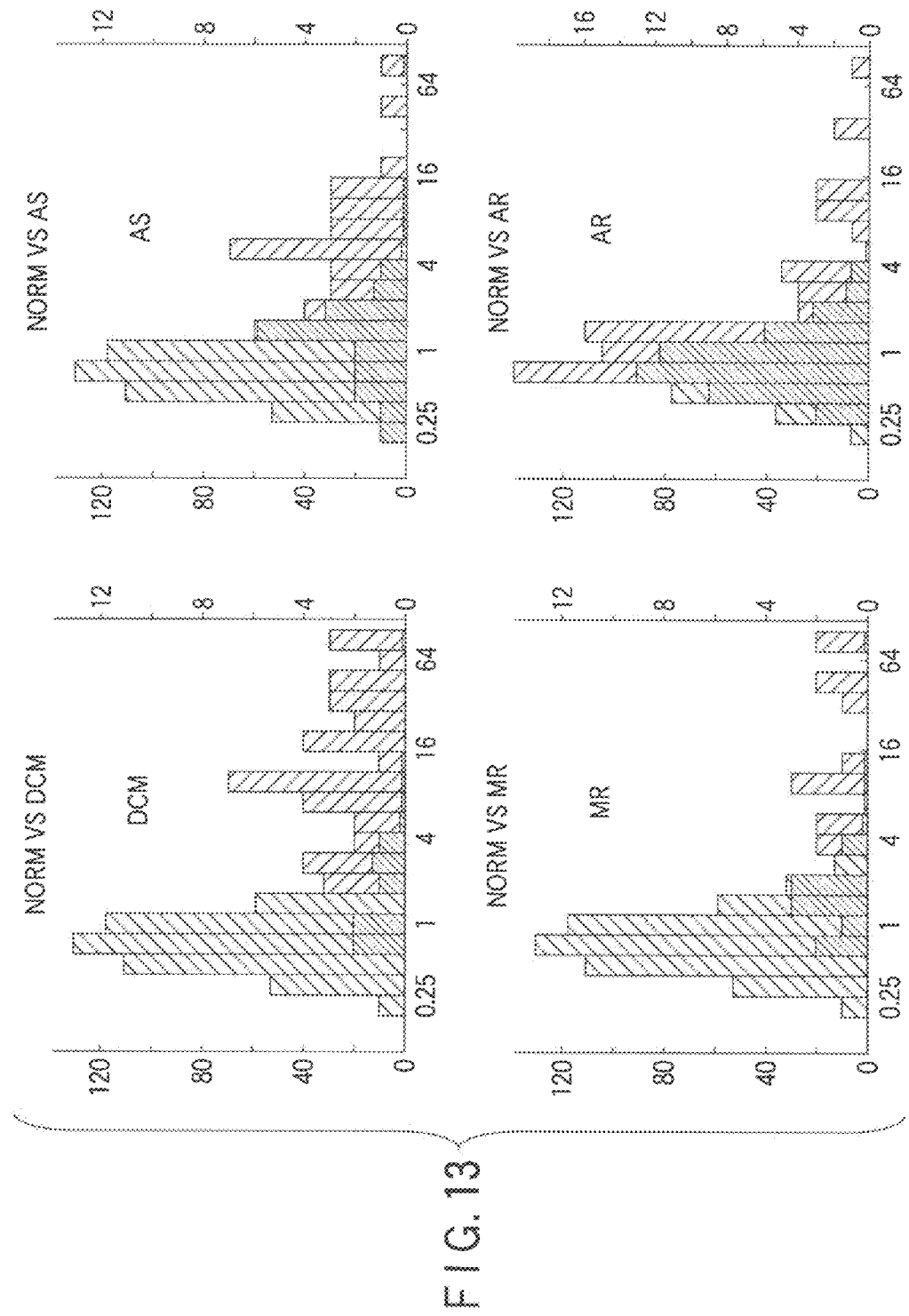
FIG. 13 is a view showing histograms for the respective diseases (DCM, MR, AS, and AR) for the evaluation of discrimination of the respective diseases relative to able-bodied persons.

FIG. 13 is a view showing the histograms for the respective diseases (DCM, MR, AS, and AR) for the evaluation of discrimination between the respective diseases and able-bodied persons. As shown in FIG. 13, it was possible to perform relatively proper separation in the cases of DCM and MR, but was difficult to perform separation in the cases of AS and AR.

Figure 14:
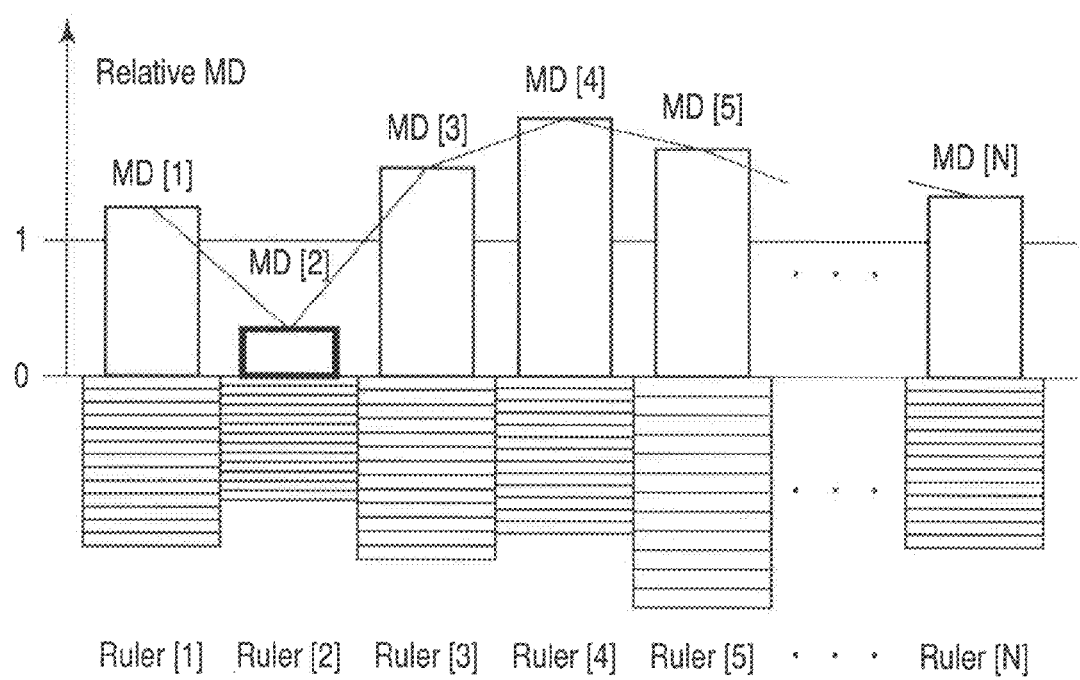
FIG. 14 is a view showing a histogram which is generated in this embodiment for each disease associated with a Mahalanobis distance (MD value).

FIG. 14 shows a histogram which is generated in this embodiment for each disease associated with a Mahalanobis distance (MD value). The Mahalanobis distances in FIG. 14 were obtained by normalizing the diagnosis index data of the object with a ruler for each disease. According to this histogram, the nearer to zero the distance, the higher the coincidence between the patient and the corresponding disease pattern. Providing such a histogram as diagnosis support information allows a user such as a doctor to pick up a disease type exhibiting a short distance as a disease candidate.

(Effects)

The above arrangement can obtain the following effects.

This medical image diagnosis support system or medical diagnosis support apparatus extracts parameters by using the automatically measured values (diagnosis indexes), image patters, waveforms, and the like obtained by automatic measurement in a medical image diagnosis apparatus such an ultrasonic diagnosis apparatus, generates rulers for the respective disease cases by using the parameters as item factors in the MT systems, determines whether a predetermined patient (i.e., a patient who is unknown whether he/she is in a normal or abnormal condition, or if he/she is in an abnormal condition, unknown about the type of disease) has a normal or abnormal health condition, or if he/she has an abnormal condition, the type of disease, and display the result as diagnosis support information in a predetermined form. It is therefore possible to quickly and easily perform normality/abnormality discrimination and disease type discrimination with high versatility while avoiding multillinarity by setting parameters using automatically measured values as item factors in the MT system based on objective quantitative values called Mahalanobis distances. In particular, when compared with the prior art using pattern recognition, this automatic diagnosis support apparatus can easily execute normality/abnormality discrimination and disease type discrimination even if a sample item factor exhibits behavior which does not belong to any past case.

In addition, this medical image diagnosis support system or medical diagnosis support apparatus displays a normality/abnormality discrimination result and disease type discrimination result in the form of a radar chart, histogram, or the like which indicates the relative distances of the respective disease types. This allows a user such as a doctor to quickly and easily make a visual check on examination results by the generation and shapes of peaks for the respective disease types.

(1) Each function associated with each embodiment can also be implemented by installing programs for executing the corresponding processing in a computer such as a workstation and mapping them in a memory. In this case, the programs which can cause the computer to execute the corresponding techniques can be distributed by being stored in recording media such as magnetic disks (floppy® disks, hard disks, and the like), optical disks (CD-ROMs, DVDs, and the like), and semiconductor memories.

(2) The above embodiment has exemplified the case in which the automatic diagnosis support system is implemented by combining the ultrasonic diagnosis apparatus 2 and the automatic diagnosis support apparatus 3. However, the medical image diagnosis apparatus to be combined with the automatic diagnosis support apparatus 3 is not limited to the ultrasonic diagnosis apparatus. For example, it is possible to use an X-ray computed tomography apparatus, magnetic resonance imaging apparatus, X-ray diagnosis apparatus, and nuclear medicine diagnosis apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An automatic diagnosis support apparatus comprising:
an extraction unit configured to extract a plurality of parameters associated with a predetermined object by using medical information associated with the object which is acquired by a medical image diagnosis apparatus and to extract the plurality of parameters for each disease associated with a disable-bodied person by using medical information associated with the disable-bodied person and acquired in advance;
a calculation unit configured to calculate a ruler associated with each disease case by executing an MT system using the plurality of parameters for each disease associated with the disable-bodied person as item factors and to calculate distances for each disease, the distances being acquired between the object and state spaces of the disable-bodied person associated with said each disease by executing the MT system using the plurality of parameters associated with the object as item factors;
a determination unit configured to determine a disease type of the object by using the ruler associated with said each disease case and the distances between the object and the state spaces of the disable-bodied person associated with said each disease;
a support information generating unit configured to generate diagnosis support information based on the determination result; and
a display unit configured to display the diagnosis support information in a predetermined form.

2. The apparatus according to claim 1, wherein the ruler is a Mahalanobis distance.

3. The apparatus according to claim 1, wherein the extraction unit extracts the plurality of parameters associated with an able-bodied person by using medical information associated with the able-bodied person which is acquired in advance,
the calculation unit calculates a ruler associated with the able-bodied person by executing the MT system using the plurality of parameters associated with the able-bodied person as item factors, and calculates a distance between the object and a state space of the able-bodied person by executing the MT system using a plurality of parameters associated with the object as item factors,
the determination unit determines, by using the ruler associated with the able-bodied person and the distance between the object and the state space of the able-bodied person, whether the object is an able-bodied person or a disable-bodied person, and
the support information generating unit generates the diagnosis support information including a determination result indicating whether the object is an able-bodied person or a disable-bodied person.

4. The apparatus according to claim 1, wherein the medical image diagnosis apparatus is an ultrasonic diagnosis apparatus.

5. The apparatus according to claim 1, wherein the predetermined parameter includes at least one of pattern recognition data associated with a B mode image, waveform pattern recognition data based on a Doppler waveform, a diagnosis index obtained by Doppler automatic measurement, and a diagnosis index based on an electrocardiogram.

6. The apparatus according to claim 1, wherein the calculation unit normalizes the ruler associated with said each disease and the distance between the object and the state space of the disable-bodied person associated with said each disease, and
the determination unit calculates a relative distance for disease discrimination by using the normalized ruler associated with said each disease case and the normalized distance between the object and the state space of the disable-bodied person associated with said each disease, and determines a disease type of the object based on the relative distance for disease discrimination.

7. The apparatus according to claim 1, wherein the support information generating unit generates, as the diagnosis support information, a radar chart using each disease as a variable.

8. The apparatus according to claim 7, wherein the support information generating unit generates the radar chart in which the nearer to a circumference a position corresponding to each disease, the higher the possibility of the disease, and which displays, as a reference, a range in which normality is estimated.

9. The apparatus according to claim 1, wherein the support information generating unit generates one of a quantitative value and a histogram to indicate a possibility of said each disease as the diagnosis support information.

10. The apparatus according to claim 1, further comprising a control unit configured to control an operation timing of the apparatus in synchronism with completion of acquisition of the medical information by the medical image diagnosis apparatus.

11. An automatic diagnosis support apparatus according to claim 1, wherein the calculation unit performs a pattern recognition process to an ultrasonic image Doppler waveform to acquire a diagnosis index as the parameter and calculates the distances by using the diagnosis index.

12. An ultrasonic diagnosis apparatus comprising:
- an ultrasonic data acquisition unit configured to acquire ultrasonic data associated with a predetermined object by scanning the object with ultrasonic waves;
- an extraction unit configured to extract a plurality of parameters associated with the object by using medical information associated with the object and including the ultrasonic data and to extract the plurality of parameters for each disease associated with a disable-bodied person by using medical information associated with the disable-bodied person and acquired in advance;
- a calculation unit configured to calculate a ruler associated with each disease case by executing an MT system using the plurality of parameters for each disease associated with the disable-bodied person as item factors and to calculate distances for each disease, the distances being acquired between the object and state spaces of the disable-bodied person associated with said each disease by executing the MT system using the plurality of parameters associated with the object as item factors;
- a determination unit configured to determine a disease type of the object by using the ruler associated with said each disease case and the distances between the object and the state spaces of the disable-bodied person associated with said each disease;
- a support information generating unit configured to generate diagnosis support information based on the determination result; and
- a display unit configured to display the diagnosis support information in a predetermined form.

13. The apparatus according to claim 12, wherein the ruler is a Mahalanobis distance.

14. The apparatus according to claim 12, wherein the extraction unit extracts the plurality of parameters associated with an able-bodied person by using medical information associated with the able-bodied person which is acquired in advance,
- the calculation unit calculates a ruler associated with the able-bodied person by executing the MT system using the plurality of parameters associated with the able-bodied person as item factors, and calculates a distance between the object and a state space of the able-bodied person by executing the MT system using a plurality of parameters associated with the object as item factors,
- the determination unit determines, by using the ruler associated with the able-bodied person and the distance between the object and the state space of the able-bodied person, whether the object is an able-bodied person or a disable-bodied person, and
- the support information generating unit generates the diagnosis support information including a determination result indicating whether the object is an able-bodied person or a disable-bodied person.

15. The apparatus according to claim 12, wherein the medical image diagnosis apparatus is an ultrasonic diagnosis apparatus.

16. The apparatus according to claim 12, wherein the predetermined parameter includes at least one of pattern recognition data associated with a B mode image, waveform pattern recognition data based on a Doppler waveform, a diagnosis index obtained by Doppler automatic measurement, and a diagnosis index based on an electrocardiogram.

17. The apparatus according to claim 12, wherein the calculation unit normalizes the ruler associated with said each disease and the distance between the object and the state space of the disable-bodied person associated with said each disease, and
- the determination unit calculates a relative distance for disease discrimination by using the normalized ruler associated with said each disease case and the normalized distance between the object and the state space of the disable-bodied person associated with said each disease, and determines a disease type of the object based on the relative distance for disease discrimination.

18. The apparatus according to claim 12, wherein the support information generating unit generates, as the diagnosis support information, a radar chart using each disease as a variable.

19. The apparatus according to claim 18, wherein the support information generating unit generates the radar chart in which the nearer to a circumference a position corresponding to each disease is, the higher the possibility of the disease, and which displays, as a reference, a range in which normality is estimated.

20. The apparatus according to claim 12, wherein the support information generating unit generates one of a quantitative value and a histogram to indicate a possibility of said each disease as the diagnosis support information.

21. The apparatus according to claim 12, further comprising a control unit configured to control an operation timing of the apparatus in synchronism with completion of acquisition of the medical information by the medical image diagnosis apparatus.

22. An automatic diagnosis support method comprising:
- extracting a plurality of parameters associated with a predetermined object by using medical information associated with the object which is acquired by a medical image diagnosis apparatus;
- extracting the plurality of parameters for each disease associated with a disable-bodied person by using medical information associated with the disable-bodied person and acquired in advance;
- calculating a ruler associated with each disease case by executing an MT system using the plurality of parameters for each disease associated with the disable-bodied person as item factors;
- calculating distances for each disease, the distances being acquired between the object and state spaces of the disable-bodied person associated with said each disease by executing the MT system using the plurality of parameters associated with the object as item factors;
- determining a disease type of the object by using the ruler associated with said each disease case and the distances between the object and the state spaces of the disable-bodied person associated with said each disease;
- generating diagnosis support information based on the determination result; and
- displaying the diagnosis support information in a predetermined form.

* * * * *